(12) United States Patent
Neville et al.

(10) Patent No.: US 9,067,968 B2
(45) Date of Patent: Jun. 30, 2015

(54) TIGHT JUNCTION PROTEIN MODULATORS AND USES THEREOF

(71) Applicant: The Regents of the University of Colorado, a body corporate, Denver, CO (US)

(72) Inventors: Margaret C. Neville, Denver, CO (US); Neal Beeman, Tucker, GA (US); Robert S. Hodges, Denver, CO (US)

(73) Assignee: The Regents of the University of Colorado, a body corporate, Denver, CO (US)

( * ) Notice: Subject to any disclaimer, the term of this patent is extended or adjusted under 35 U.S.C. 154(b) by 0 days.

(21) Appl. No.: 14/059,214

(22) Filed: Oct. 21, 2013

(65) Prior Publication Data

US 2014/0045768 A1 Feb. 13, 2014

Related U.S. Application Data

(63) Continuation of application No. 12/743,816, filed as application No. PCT/US2008/841000 on Nov. 19, 2008, now Pat. No. 8,563,515.

(60) Provisional application No. 60/988,865, filed on Nov. 19, 2007.

(51) Int. Cl.
| | |
|---|---|
| *A61K 38/00* | (2006.01) |
| *C07K 14/705* | (2006.01) |
| *A61K 38/16* | (2006.01) |
| *A61K 38/08* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07K 7/06* | (2006.01) |
| *A61K 38/07* | (2006.01) |
| *A61K 38/17* | (2006.01) |

(52) U.S. Cl.
CPC . *C07K 7/06* (2013.01); *A61K 38/07* (2013.01); *A61K 38/177* (2013.01)

(58) Field of Classification Search
CPC ......... A61K 38/07; A61K 38/177; C07K 7/06
See application file for complete search history.

(56) References Cited

U.S. PATENT DOCUMENTS 6,248,864 B1 * 6/2001 Blaschuk et al. ............. 530/317
8,563,515 B2 * 10/2013 Neville et al. ................ 514/19.1

OTHER PUBLICATIONS

Luomanen. Ora focal epithelial hyperplasia removed with CO2 laser. Int J Oral Maxillofac Surg 1990, vol. 4, abstract only, 1 page.*
Crighton et al. DRAM, a p53-induced modulator of autophagy, is critical for apoptosis. Cell. 2006, vol. 126, No. 1, pp. 121-134.*

* cited by examiner

*Primary Examiner* — Marcela M Cordero Garcia
(74) *Attorney, Agent, or Firm* — Don D. Cha; Hamilton DeSanctis & Cha, LLP

(57) ABSTRACT

The invention provides tight junction protein modulators, compositions comprising the same, and uses thereof. In particular, the invention provides tight junction protein modulators that modulate the second extracellular loop of tight junction proteins, such as occludin or claudin.

7 Claims, 7 Drawing Sheets

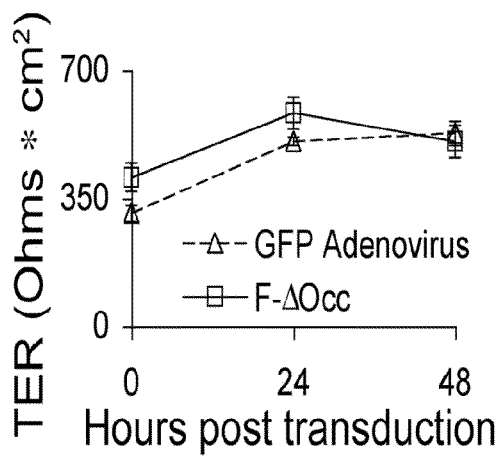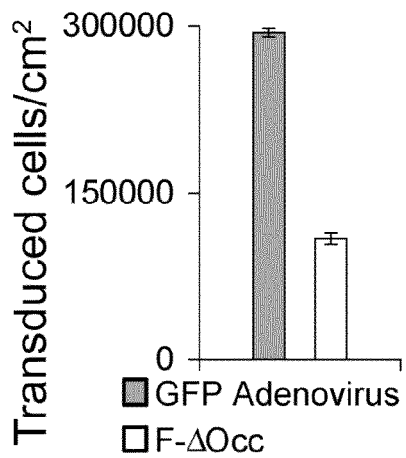
FIGURE 2A
FIGURE 2B
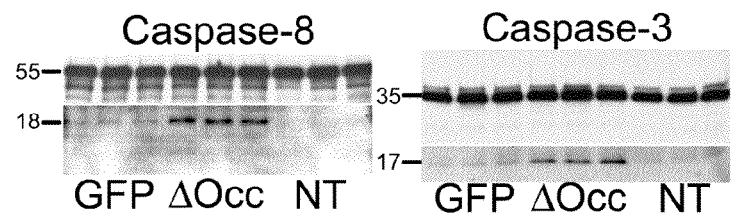
FIGURE 2C
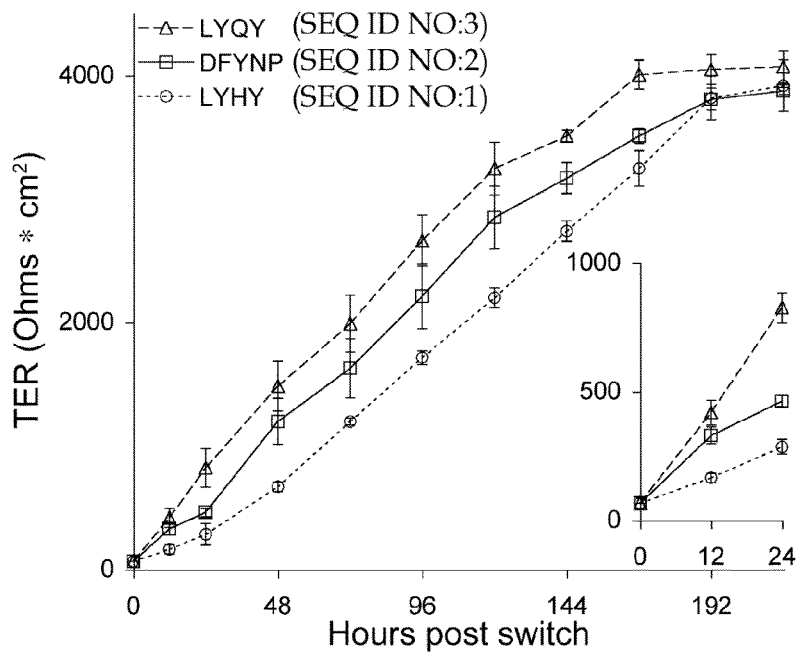
FIGURE 3A

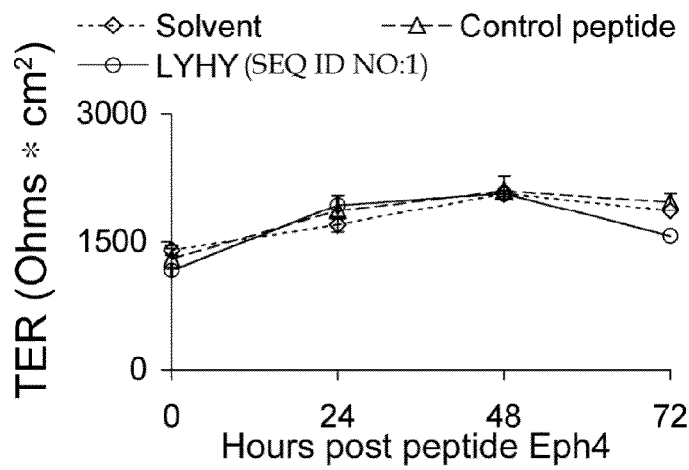
FIGURE 4B
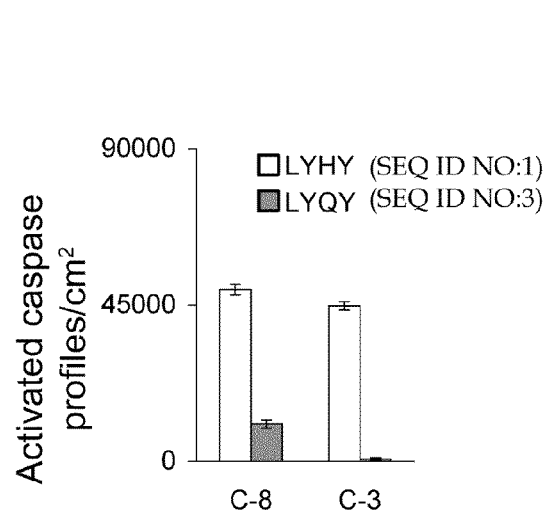
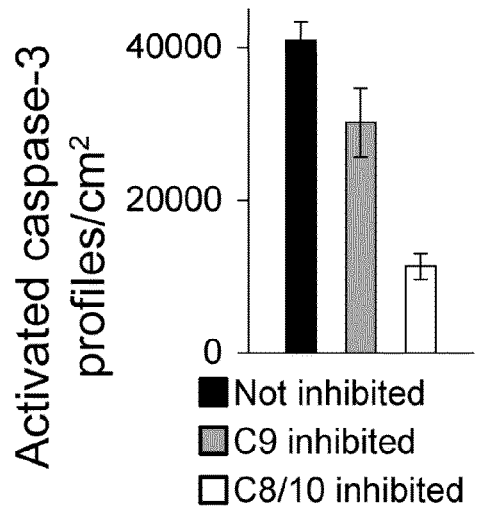
FIGURE 5A
FIGURE 5B
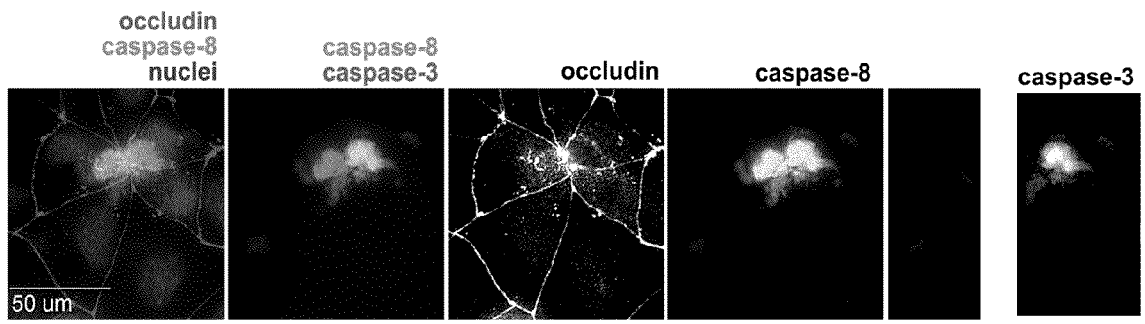
FIGURE 6

SEQUENCE LISTING

<160> NUMBER OF SEQ ID NOS: 11

<210> SEQ ID NO 1
<211> LENGTH: 4
<212> TYPE: PRT
<213> ORGANISM: Artificial Sequence
<220> FEATURE:
<223> OTHER INFORMATION: TJ Protein Modulator 1

<400> SEQUENCE: 1

Leu Tyr His Tyr
1

<210> SEQ ID NO 2
<211> LENGTH: 5
<212> TYPE: PRT
<213> ORGANISM: Artificial Sequence
<220> FEATURE:
<223> OTHER INFORMATION: TJ Protein Modulator 2

<400> SEQUENCE: 2

Asp Phe Tyr Asn Pro
1               5

<210> SEQ ID NO 3
<211> LENGTH: 4
<212> TYPE: PRT
<213> ORGANISM: Artificial Sequence
<220> FEATURE:
<223> OTHER INFORMATION: Control Peptide Fig. 3A

<400> SEQUENCE: 3

Leu Tyr Gln Tyr
1

<210> SEQ ID NO 4
<211> LENGTH: 6
<212> TYPE: PRT
<213> ORGANISM: Artificial Sequence
<220> FEATURE:
<223> OTHER INFORMATION: Linear Artificial Peptide 1

<400> SEQUENCE: 4

Cys Leu Tyr His Tyr Cys
1               5

<210> SEQ ID NO 5
<211> LENGTH: 7
<212> TYPE: PRT
<213> ORGANISM: Artificial Sequence
<220> FEATURE:
<223> OTHER INFORMATION: Linear Artificial Peptide 2

<400> SEQUENCE: 5

Cys Asp Phe Tyr Asn Pro Cys
1               5

<210> SEQ ID NO 6
<211> LENGTH: 7
<212> TYPE: PRT
<213> ORGANISM: Artificial Sequence
<220> FEATURE:
<223> OTHER INFORMATION: Linear Peptide 4

<400> SEQUENCE: 6

Gly Asp Phe Tyr Asn Pro Gly
1               5

```
<210> SEQ ID NO 7
<211> LENGTH: 7
<212> TYPE: PRT
<213> ORGANISM: Artificial Sequence
<220> FEATURE:
<223> OTHER INFORMATION: Example 2: Active Peptide
<220> FEATURE:
<221> NAME/KEY: DISULFID
<222> LOCATION: (1)..(7)
<223> OTHER INFORMATION: Disulfide linkage between Cysteines of
      Positions 1 and 7

<400> SEQUENCE: 7

Cys Asp Phe Tyr Asn Pro Cys
1               5

<210> SEQ ID NO 8
<211> LENGTH: 7
<212> TYPE: PRT
<213> ORGANISM: Artificial Sequence
<220> FEATURE:
<223> OTHER INFORMATION: Example 2: Different End Group Peptide 1
<220> FEATURE:
<221> NAME/KEY: DISULFID
<222> LOCATION: (1)..(7)
<223> OTHER INFORMATION: Disulfide Linkage between Cysteines in
      Positions 1 and 7
<220> FEATURE:
<221> NAME/KEY: MOD_RES
<222> LOCATION: (1)..(1)
<223> OTHER INFORMATION: ACETYLATION

<400> SEQUENCE: 8

Cys Asp Phe Tyr Asn Pro Cys
1               5

<210> SEQ ID NO 9
<211> LENGTH: 7
<212> TYPE: PRT
<213> ORGANISM: Artificial Sequence
<220> FEATURE:
<223> OTHER INFORMATION: Example 2: Different End Group Peptide 2
<220> FEATURE:
<221> NAME/KEY: DISULFID
<222> LOCATION: (1)..(7)
<223> OTHER INFORMATION: Disulfide linkage between Cysteines in
      Positions 1 and 7
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: Linked to an Amide

<400> SEQUENCE: 9

Cys Asp Phe Tyr Asn Pro Cys
1               5

<210> SEQ ID NO 10
<211> LENGTH: 7
<212> TYPE: PRT
<213> ORGANISM: Artificial Sequence
<220> FEATURE:
<223> OTHER INFORMATION: Example 2: D-Amino Acid peptide
<220> FEATURE:
<221> NAME/KEY: MISC_FEATURE
<222> LOCATION: (1)..(7)
<223> OTHER INFORMATION: All D-Amino Acids
<220> FEATURE:
<221> NAME/KEY: DISULFID
<222> LOCATION: (1)..(7)
```

```
-continued

<223> OTHER INFORMATION: Disulfide Linkage between Cysteines in
      Positions 1 and 7

<400> SEQUENCE: 10

Cys Asp Phe Tyr Asn Pro Cys
1               5

<210> SEQ ID NO 11
<211> LENGTH: 7
<212> TYPE: PRT
<213> ORGANISM: Artificial Sequence
<220> FEATURE:
<223> OTHER INFORMATION: Glycine terminated peptide
<220> FEATURE:
<221> NAME/KEY: MISC_FEATURE
<222> LOCATION: (2)..(2)
<223> OTHER INFORMATION: aspartic acid, glutamic acid, asparagine,
      or glutamine
<220> FEATURE:
<221> NAME/KEY: MISC_FEATURE
<222> LOCATION: (3)..(3)
<223> OTHER INFORMATION: phenylalanine, tyrosine, tryptophan, or
      leucine
<220> FEATURE:
<221> NAME/KEY: MISC_FEATURE
<222> LOCATION: (4)..(4)
<223> OTHER INFORMATION: tyrosine, phenylalanine, tryptophan, or
      leucine
<220> FEATURE:
<221> NAME/KEY: MISC_FEATURE
<222> LOCATION: (5)..(5)
<223> OTHER INFORMATION: asparagine or glutamine
<220> FEATURE:
<221> NAME/KEY: MISC_FEATURE
<222> LOCATION: (6)..(6)
<223> OTHER INFORMATION: proline

<400> SEQUENCE: 11

Gly Xaa Xaa Xaa Xaa Xaa Gly
1               5
```

TIGHT JUNCTION PROTEIN MODULATORS AND USES THEREOF

CROSS-REFERENCE TO RELATED APPLICATIONS

This application is continuation of U.S. patent application Ser. No. 12/743,816, filed Jul. 30, 2010, which is a National Stage Application of PCT Patent Application No. PCT/US08/84100, filed Nov. 19, 2008, which claims the priority benefit of U.S. Provisional Application No. 60/988,865, filed Nov. 19, 2007, all of which are incorporated herein by reference in their entirety.

STATEMENT REGARDING FEDERALLY FUNDED RESEARCH

This invention was made with government support under grant number HD038129 awarded by the National Institutes of Health. The government has certain rights in the invention.

FIELD OF THE INVENTION

The invention relates to tight junction protein modulators, compositions comprising the same, and uses thereof. In particular, the invention relates to peptide modulators of tight junction proteins that mimic or modulate the second extracellular loop of claudins or occludins.

BACKGROUND OF THE INVENTION

Organs and fluid spaces throughout the bodies of animals are lined by polarized epithelia that serve, in part, to modify the apical and basolateral fluid compartments. In order for these organs and fluid spaces to function, it is necessary that the apical and basolateral fluid compartments be kept physiologically separated, so as to maintain the modifications imparted by the epithelia. This physiological separation is maintained by the tight junction, classically known as the zonula occludens.

The tight junction is an unbroken intercellular junction formed by an anastomosing network of protein and lipid strands that apically circumscribes every luminal epithelial cell. This intercellular adhesion complex is a continuous molecular seal between all of the luminal epithelial cells and forms a selective barrier to paracellular, and thereby transepithelial, solute flux and ionic current (i.e., the gate function). The tight junction is also believed to maintain the distinct lipid and protein composition of the apical and basolateral cellular membranes (i.e., the fence function). The gate and fence functions of the tight junction thus polarize the unit epithelial cell and the epithelium itself at the same physical plane. Occludin and the claudins help to form, and are localized within, tight junction strands where they participate in homophilic and/or heterophilic interactions between adjacent cells. As schematically illustrated in FIG. 1A, occludin and the claudins are tetraspanin proteins, having intracellular N and C termini, two extracellular loops, and four transepithelial domains, and have been shown to be involved in establishing and maintaining the physiological properties of the tight junction.

In addition to physiological barrier roles, the tight junction regulates many aspects of intracellular behavior. For example, the tight junction has been shown to be involved in the cell cycle arrest attendant on contact inhibition. Tight junction disruption induces epithelial to mesenchymal transition, increases cellular motility, produces overgrowth of cultured cells, and increases tumorigenicity of cells transplanted into animals. Several tight junction proteins regulate transcription. Tight junction formation is also involved in the inter-related phenomena of development of cellular polarity and epithelial differentiation.

The physiological barrier functions as well as the regulatory activities of the tight junction must be maintained in epithelia whose cellular populations are undergoing constant turnover throughout the life of the organism. In this process individual epithelial cells are extruded apically and undergo apoptosis in a manner that does not alter the electrical resistance or tracer flux across the epithelium.

Higher levels of apoptosis induced in epithelia during experiments or during pathological states have been shown to alter barrier properties. Disruption of occludin has been shown in a number of studies to disrupt the physiological and structural properties of the tight junction. A 19 amino acid second extracellular loop sequence peptide mimic of occludin impeded recovery of tight junction structure following a short period of incubation with a calcium-free solution (the calcium switch) in T84 intestinal epithelial cells.

Isolated patches of cells throughout treated monolayers showed punctate, intracellular distributions of the tight junction proteins ZO-1, occludin, claudin-1, and JAM-A. A similar peptide was used to treat the EPH4 mammary epithelial cell line leading to punctate, intracellular, non-tight junctional distribution of occludin in isolated patches of cells throughout treated monolayers. Another similar peptide was shown to disrupt barrier function in a sertoli cell line. This same peptide shut down spermatogenesis and decreased testicular weight when injected into the testicular lumen of rats. The relationship between occludin disruption and cellular survival has not been widely studied. However, disruption of several types of cellular adhesion proteins; integrins, cadherins, and connexins has been reported to stimulate apoptosis. Interestingly, epithelial cell lines derived from the occludin knockout mouse showed decreased survival signaling and increased apoptotic rates.

Although most tumors are devoid of tight junctions, many tight junction proteins, particularly claudins 3, 4 and 7 are found at high levels in tumors of epithelial origin where their function and localization are presently unknown.

Although tight junction protein modulators are known, these are not without any problems. Therefore, there is a continuing need for other tight junction protein modulators.

SUMMARY OF THE INVENTION

The present invention relates to tight junction protein modulators, compositions comprising the same, and uses thereof. In particular, the invention relates to peptide modulators of tight junction proteins that mimic or modulate the second extracellular loop of claudins or occludin, and methods for using the same.

In particular, some aspects of the invention provide a method for modulating apoptosis of epithelial cells of a subject comprising administering to the subject a therapeutically effective amount of a tight junction protein modulator.

In some embodiments, the tight junction protein modulator causes internalization of the tight junction protein occludin or claudin. In other embodiments, the tight junction protein modulator stimulates or causes apoptosis of epithelial cells.

There are various clinical conditions associated with abnormal apoptosis of epithelial cells including cancer, such as skin cancer, breast cancer, ovarian cancer, and metastases thereof. Thus, in some embodiments, methods of the invention are useful in treating a subject who suffers from cancer.

Yet in other embodiments, the tight junction protein modulator modulates an adhesion protein. Exemplary adhesion proteins that can be modulated by methods of the invention include occludin, claudin, junction adhesion molecule, integrins, or a combination thereof. In some embodiments, the tight junction protein protein modulator modulates occludin, claudin, or a combination thereof.

In other embodiments, the tight junction protein modulator comprises at least 3 consecutive amino acid sequences of the second extracellular loop sequence of occludin or claudin, or a derivative thereof. Within these embodiments, in some instances, the tight junction protein modulator comprises amino acid sequences of LYHY (SEQ ID NO:1), DFYNP (SEQ ID NO:2), or a derivative thereof. Still in other instances, the tight junction protein modulator comprises D-amino acids. Yet in other instances, the tight junction protein modulator comprises about 20 amino acid sequences or less and is a cyclic peptide or a linear peptide, or a derivative thereof.

In one particular embodiment, the tight junction protein modulator is of the formula:

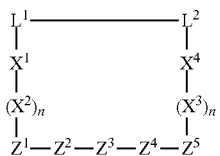

I wherein
each of $X^1$ and $X^4$ is independently cysteine, glutamic acid, aspartic acid, lysine, or ornithine;
each of $L^1$ and $L^4$ is independently the corresponding functional group of the amino acid side chain of $X^1$ and $X^4$, respectively, or $-(CH_2)_m-$;
each of $X^2$ and $X^3$ is glycine;
m is an integer from 1 to 4;
each n is independently 0, 1 or 2;
$Z^1$ is aspartic acid, glutamic acid, asparagine, or glutamine;
$Z^2$ is phenylalanine, tyrosine, tryptophan, or leucine;
$Z^3$ is tyrosine, phenylalanine, tryptophan, or leucine;
$Z^4$ is asparagine or glutamine; and
$Z^5$ is proline.

It should be appreciated that amino acids are often identified by a single letter codes such as P for proline and C for cysteine. As shown above, however, in some instances within this disclosure, such a single code can also represent amino acids that are known to be "interchangeable" or have a similar side-chain. Thus, while F typically represents phenylalanine, it can also represent tyrosine, tryptophan, or glutamine. Thus, unless explicitly stated or the context requires otherwise it is to be understood that the single letter amino acid codes includes amino acids having a similar side-chain or are known to be interchangeable by one skilled in the art.

Within Compounds of Formula I, in some instances $Z^1$ is aspartic acid, $Z^2$ is phenylalanine, $Z^3$ is tyrosine, and $Z^4$ is asparagine. In other instances, $X^1$ and $X^4$ are cysteine. In such instances, often $L^1$ and $L^2$ together is a moiety of the formula —S—S—.

Other aspects of the invention provide methods for removing at least a portion of epithelia cells from a subject. Generally such methods include causing apoptosis of the epithelia cells; however, it should be appreciated that methods can also simply involve disrupting the tight junction protein to cause removal of adhesion between epithelial cells. Such methods typically comprise administering to the subject in need of such treatment a tight junction protein inhibitor. In some embodiments, the epithelia cells are in hyperplastic stages. In one particular instance, the epithelia cells are in the subject's breast. In such instance, the tight junction protein can be administered to the subject by intraductal injection.

Still other aspects of the invention provide a compound comprising 20 (typically 10, often 6) amino acid sequences or less and at least 3 consecutive amino acid sequences of the second extracellular loop sequence of occludin or claudin, or a derivative thereof. In some embodiments, the compound comprises amino acid sequences of LYHY(SEQ ID NO:1), DFYNP (SEQ ID NO:2), or a derivative or a combination thereof.

Still in other embodiments, the compound comprises a cyclic peptide, D-amino acid sequences, or a combination thereof. Within these embodiments, in some instances the cyclic peptide is of the formula:

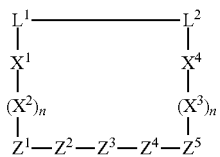

wherein
each of $X^1$ and $X^4$ is independently cysteine, glutamic acid, aspartic acid, lysine, or ornithine;
each of $L^1$ and $L^4$ is independently the corresponding functional group of the amino acid side chain of $X^1$ and $X^4$, respectively, or $-(CH_2)_m-$;
each of $X^2$ and $X^3$ is glycine;
m is an integer from 1 to 4;
each n is independently 0, 1 or 2;
$Z^1$ is aspartic acid, glutamic acid, asparagine, or glutamine;
$Z^2$ is phenylalanine, tyrosine, tryptophan, or leucine;
$Z^3$ is tyrosine, phenylalanine, tryptophan, or leucine;
$Z^4$ is asparagine or glutamine; and
$Z^5$ is proline.

Yet other aspects of the invention provide methods for treating a clinical condition associated with abnormal apoptosis of epithelial cells in a subject, said method comprising administering to the subject in need of such a treatment a composition a therapeutically effective amount of a tight junction protein modulator. In some embodiments, the tight junction protein modulator stimulates apoptosis of epithelial cells.

Any clinical condition associated with abnormal apoptosis of epithelial cells can be treated by methods of the invention. In some embodiments, methods of the invention are used to treat a clinical condition that comprises skin cancer, breast cancer, ovarian cancer, or metastases thereof.

In other embodiments, the tight junction protein modulator modulates an adhesion protein. Suitable adhesion proteins include, but are not limited to, occludin, claudin, junction adhesion molecule, integrins, or a combination thereof. In some instances, the adhesion protein comprises occludin, claudin, or a combination thereof. In other instances, the tight junction protein modulator comprises at least 3 consecutive amino acid sequences of the second extracellular loop sequence of occludin or claudin, or a derivative thereof. In some cases, the amino acid comprises at least one D-amino acid.

BRIEF DESCRIPTION OF THE DRAWINGS

FIG. 2A is a graph of counts of remaining transduced cells (GFP positive) at 48 hours post transduction.

FIG. 2B is a graph of transepithelial resistance (TER) of cultures at 24 and 48 hours post-transduction.

FIG. 2C is western blots showing activation of caspases 8 and 3 in transduced cells.

FIG. 3A is a graph showing recovery of transepithelial resistance after calcium switch in the presence of control peptide (LYQY (SEQ ID NO:3)), claudin peptide (DFYNP (SEQ ID NO:2)) and occludin peptide (LYHY (SEQ ID NO:1)). The inset is a magnification of the first 24 hours of this graph.

FIG. 4B is a graph of TER that was recorded at 0, 24, 28, and 72 hours post peptide treatment of EPH4 cells that were grown on filters until the TER reached 1000 (Ohms·cm$^2$), then treated with solvent, LYHY (SEQ ID NO:1), or control peptides.

FIG. 5A is a graph showing the number of EPH4 cells showing caspase-3 (C-3) and caspase 8 (C-8) activation after 2 hours of treatment with the LYHY (SEQ ID NO:1) peptide or the control LYQY (SEQ ID NO:3) peptide.

FIG. 5B is a graph showing the number of EPH4 cells showing caspase-3 activation in the presence of inhibitors of caspase-8 or caspase-9.

FIG. 6 is an immunofluorescence image of mature EPH4 monolayers grown on glass slides that were treated with LYHY (SEQ ID NO:1) peptide at 350 μM for 2 hours and stained live during peptide treatment for activated caspase-8 and activated caspase-3.

DETAILED DESCRIPTION OF THE INVENTION

Figure 1A:
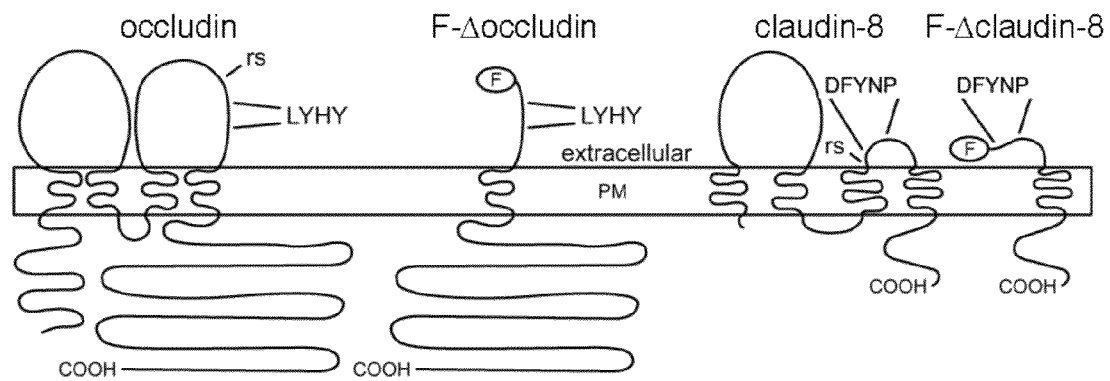
FIG. 1A is the schematic illustration of general topology of occludin occludin and claudin 8 showing the mouse sequences used to make tight junction disrupting constructs and peptides.

The tight junction regulates inter alia permeability across epithelia and maintains distinct apical and basal regions of unit epithelial cells. While known to interact with various signaling molecules and to regulate intracellular behavior, the tight junction has not been reported to regulate apoptosis. The present inventors have found that disrupting the tight junction protein occludin, e.g., by dominant-negative occludin or claudin expression and externally applied function-blocking peptides, mimicked loss of occludin function in otherwise normal epithelial cells that are unable to form or maintain occludin binding or have undergone cellular dysregulation disruptive of occludin function. This disruption increased apoptosis. Caspases-8 and 3 were activated within minutes of occludin disruption. Caspase-8 inhibition, but not caspase-9 inhibition, prevented caspase-3 activation, indicating that apoptosis was induced via elements of the death receptor pathway. Occludin disruption lead to movement of endogenous occludin out of the junctional complex where it localized with elements of the death inducing signaling complex; Fas, FADD, and activated caspase-8. Cells showing tight junctional disruption were extruded from the monolayer without any significant loss of transepithelial electrical resistance during a several fold increase in apoptotic rate.

The present inventors have also found that occludin disruption led to an increase in the rate of cellular removal and apoptosis. Moreover, the present inventors discovered that caspase-8 was activated within minutes of occludin disruption and that caspase-8 activation preceded caspase-3 activation during treatment with an occludin function blocking peptide. As disclosed herein, activation of caspase-8 was achieved by elements of the death inducing signaling complex (DISC). Moreover, the physiological property of transepithelial electrical resistance remained stable during the several-fold increase of cellular extrusion and apoptosis.

Disruption of endogenous occludin function was used to mimic loss of occludin function in otherwise normal epithelial cells that are spatially unable to form or maintain occludin binding or have undergone any cellular dysregulation disruptive of occludin function. The present inventors have discovered that occludin disruption in cultured epithelial monolayers led to an increase in the rate of cellular removal and apoptosis. In addition, the present inventors discovered that caspase-8 was activated within minutes of occludin disruption. Moreover, in many instances caspase-8 activation preceded caspase-3 activation during treatment with an occludin function blocking peptide. Furthermore, the present inventors observed activation of caspase-8 by elements of the death inducing signaling complex (DISC). It was also observed that the physiological property of transepithelial electrical resistance remained stable during the several-fold increase of cellular extrusion and apoptotic rate seen during the experiments.

Two occludin-disrupting and two claudin-disrupting tools each were used to disrupt occludin function in three epithelial cell lines; it was found that this disruption increased apoptosis in treated cells. Apoptotic cells were lost from the monolayer with no significant change in TER. Movement of occludin out of the junctional complex in response to an occludin peptide mimic led to activation of caspase-8 in these same regions that were enriched in displaced occludin and DISC proteins.

It is believed that otherwise normal epithelial cells that are unable to form, or that lose, any of the more widely studied forms of cellular attachments undergo apoptosis. Accordingly, it is expected that disruption of integrin-mediated cell-to-substratum attachment, disruption of cadherin-mediated adherens junctions, and disruption of connexin-mediated gap junctions all stimulate apoptosis. These apoptotic responses to the disruption of cellular attachments provide an adaptive advantage to the host allowing epithelia to remove malfunctioning cells. The present inventors observed that disruption of occludin or claudin function by several means in confluent epithelial monolayers likewise leads to apoptosis.

Occludin was the first tight junction adhesion protein discovered. However, until the discovery by the present inventors, no one has recognized disruption of tight junction adhesion protein leads to apoptosis. When intact monolayers of the EPH4 cell line were treated with an occludin second extracellular loop peptide, isolated patches of cells throughout the monolayer showed a punctate, intracellular, non junctional distribution of occludin. While these peptide treated cells maintained the majority of TER seen in untreated controls, TER was reduced. An occludin second extracellular loop peptide mimic impeded recovery of TER and caused internalization of several tight junction transepithelial proteins following the calcium switch in human intestinal epithelial cells. Similar results were obtained in a rat sertoli cell line. Moreover, intratesticular injection of an occludin mimic peptide shut down spermatogenesis and decreased testis weight more than three fold.

Cell death was recently reported in epithelial cells treated with an occludin first extracellular loop peptide mimic. Peptide treatment reduced TER and increased solute permeability of treated cells. Cell death was ascertained via increased release of lactose dehydrogenase in treated cells. No attempt was made to ascertain either the rate of cell death or whether cell death was necrotic or apoptotic. More significantly, no report of apoptosis by disrupting the second extracellular loop of occludin has been reported to date.

Cells expressing dominant negative occludin appeared to migrate out of the monolayer prior to becoming TUNEL positive. The present inventors have observed that many of the occludin peptide treated cells that showed non junctional occludin distribution and caspase-8 activation also showed the distinctive morphology of cellular extrusion. The finding that the several fold increase in apoptosis did not decrease the trans-epithelial resistance indicates that cell loss proceeds by an orderly biological process that maintains rather than disrupts epithelial barrier properties. Similarly, cultured monolayers of intestinal epithelial cells were able to maintain about 50% of basal TER when treated with a Fas crosslinking antibody that led to the loss of half of the cells in the culture in only 24 hours.

Occludin and claudin peptides caused occludin to stain in intracellular, punctate, nonjunctional patches in islands of cells throughout the monolayers, while the majority of treated cells showed normal occludin localization. In several of the experiments, dominant negative occludin was expressed in only a minority of cells. These conditions should mimic loss of occludin function in otherwise normal epithelial cells that are spatially unable to form or maintain occludin binding or have undergone any cellular dysregulation disruptive of occludin function, indicating that an endogenous pathway is triggered to remove epithelial cells unable to maintain occludin function. Without being bound by any theory, it is believed that this pathway is an adaptive defense against epithelial disruption.

It is believed that disruption of occludin function initiates the death receptor pathway of apoptosis. Several studies showed that disruption of integrin function and disruption of cadherin function caused caspase-8 activation. The present inventors have discovered that elements of the death receptor or extrinsic apoptotic pathway function generally to trigger apoptosis in epithelial cells that have lost normal cell-cell attachments. The present inventors have also discovered that a specific caspase-containing complex was formed during loss of normal cellular attachment occurring prior to changes that lead to nuclear condensation and cell extrusion.

The localization of activated caspase-8 in regions of non junctional occludin indicates that displaced occludin acts to promote caspase-8 activation, as appears to be the case for unligated integrin in detachment-induced apoptosis or anoikis. The Akt antagonist, lipid phosphatase PTEN is another candidate molecule for linking loss of occludin function to apoptosis. It has been demonstrate that the PIP3 phosphatase PTEN binds to the tight junction associated MAGI, PAR, and DLG proteins. The lipid phosphatase activity of PTEN correlates positively with the stability of the apical junction complex. Moreover, PTEN plays a role in activation of the death receptor pathway of apoptosis under various conditions. The present inventors have also discovered that PTEN is associated with the tight junction (data not shown).

One of the necessary steps in the metastatic process is disruption of intercellular junctions without subsequent apoptosis. Without being bound by any theory, it is believed that the molecular pathway(s) linking occludin or claudin disruption to apoptosis is attenuated or absent in epithelial cancers, as is the case with more widely studied cellular adhesion proteins. The molecular pathways linking occludin or claudin dysregulation to metastases can be augmented by drug therapies to induce apoptosis or halt epithelial to mesenchymal transformation specifically in cells that have lost normal occludin or claudin based adhesion.

Pharmaceutical Compositions

The compounds of the present invention can be administered to a patient to achieve a desired physiological effect. Preferably the patient is an animal, more preferably a mammal, and most preferably a human. The compound can be administered in a variety of forms adapted to the chosen route of administration, i.e., orally or parenterally. Parenteral administration in this respect includes administration by the following routes: intravenous; intramuscular; subcutaneous; intraocular; intrasynovial; transepithelially including transdermal, ophthalmic, sublingual and buccal; topically including ophthalmic, dermal, ocular, rectal and nasal inhalation via insufflation and aerosol; intraperitoneal; and rectal systemic.

The active compound can be orally administered, for example, with an inert diluent or with an assimilable edible carrier, or it can be enclosed in hard or soft shell gelatin capsules, or it can be compressed into tablets, or it can be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparation can contain at least 0.1% of active compound. The percentage of the compositions and preparation can, of course, be varied and can conveniently be between about 1 to about 10% of the weight of the unit. The amount of active compound in such therapeutically useful compositions is such that a suitable dosage will be obtained. Preferred compositions or preparations according to the present invention are prepared such that an oral dosage unit form contains from about 1 to about 1000 mg of active compound.

The tablets, troches, pills, capsules and the like can also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin can be added or a flavoring agent such as peppermint, oil of wintergreen, or cherry flavoring. When the dosage unit form is a capsule, it can contain, in addition to materials of the above type, a liquid carrier. Various other materials can be present as coatings or to otherwise modify the physical form of the dosage unit. For instance, tablets, pills, or capsules can be coated with shellac, sugar or both. A syrup or elixir can contain the active compound, sucrose as a sweetening agent, methyl and propylparabens a preservatives, a dye and flavoring such as cherry or orange flavor. Of course, any material used in preparing any dosage unit form should be pharmaceutically pure and substantially non-toxic in the amounts employed. In addition, the active compound can be incorporated into sustained-release preparations and formulation.

The active compound can also be administered parenterally. Solutions of the active compound as a free base or pharmacologically acceptable salt can be prepared in water suitably mixed with a surfactant such as hydroxypropylcellulose. Dispersion can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It can be stable under the conditions of manufacture and storage and must be preserved against the contaminating action of microorganisms such as bacterial and fungi. The carrier can be a solvent of dispersion medium containing, for example, water, ethanol, polyol (e.g., glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, e.g., sugars or sodium chloride. Prolonged absorption of the injectable compositions of agents delaying absorption, e.g., aluminum monostearate and gelatin.

Sterile injectable solutions are prepared by incorporating the active compound in the required amount in the appropriate solvent with various other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique which yield a powder of the active ingredient plus any additional desired ingredient from previously sterile-filtered solution thereof.

The therapeutic compounds of the present invention can be administered to a mammal alone or in combination with pharmaceutically acceptable carriers, as noted above, the proportion of which is determined by the solubility and chemical nature of the compound, chosen route of administration and standard pharmaceutical practice.

Furthermore, compounds of the invention can be administered in combination with other pharmaceutically active compound, such as other anticancer compound, anti-inflammatory compound, or a combination thereof. Such co-administration of pharmaceutically active compound can lead to synergistic effects.

The physician will determine the dosage of the present therapeutic agents which will be most suitable for prophylaxis or treatment and it will vary with the form of administration and the particular compound chosen, and also, it will vary with the particular patient under treatment. The physician will generally wish to initiate treatment with small dosages by small increments until the optimum effect under the circumstances is reached. The therapeutic dosage can generally be from about 0.1 to about 1000 mg/day, and preferably from about 10 to about 100 mg/day, or from about 0.1 to about 50 mg/Kg of body weight per day and preferably from about 0.1 to about 20 mg/Kg of body weight per day and can be administered in several different dosage units. Higher dosages, on the order of about 2× to about 4×, may be required for oral administration.

Additional objects, advantages, and novel features of this invention will become apparent to those skilled in the art upon examination of the following examples thereof, which are not intended to be limiting.

EXAMPLES

Materials and methods

| ABBREVIATION | NAME |
|---|---|
| Fmoc | Fluorenylmethoxycarbonyl |
| HOBt | 1-Hydroxybenzotriazole monohydrate |
| DIC | Diisopropylcarbodiimide |
| DMF | N,N-Dimethylformamide |
| TFA | Trifluoroacetic acid |
| Trt | Trityl |
| tBu | t-Butyl |
| OtBu | t-Butoxy |

Antibodies:

Various antibodies were obtained as follows: Anti occludin, Zymed® clone OCOC-3F10; anti Fas, BD Biosciences clone 13; anti ZO-1, Chemicon® MAB1520; anti FADD, USBiological clone 12E7; anti MUC1, Abcam Inc. clone EP1024Y; anti-caspase-3, Cell Signaling Technology® (8G10); anti-caspase-8, Axxora® (1G12).

Cells and Cell Culture:

CIT3 mouse mammary epithelial cells were grown as described by Toddywalla V S et al., *J. Pharmacol. Exp. Ther.*, 1997, 280, 669-676. To differentiate cells, this growth medium was modified by removal of EGF and addition of 3 µg/ml each of ovine prolactin and hydrocortisone (differentiation media).

EPH4 mouse mammary epithelial cells were grown as described by Reichmann E. et al., *J. Cell Biol.*, 1989, 108, 1127-1138. To differentiate cells, this growth medium was modified by addition of 3 µg/ml each of ovine prolactin and hydrocortisone (differentiation media).

MDCK cells were grown in MEM with 2 mM L-glutamine and Earle's BSS adjusted to contain 1.5 g/L sodium bicarbonate, 0.1 mM non-essential amino acids, 1.0 mM sodium pyruvate, and 10% FBS. To differentiate cells, this growth medium was modified by addition of 3 µg/ml each of ovine prolactin and hydrocortisone (differentiation media) to that described by Peixoto E B et al., *Cell Biol. Int.*, 2006, 30, 101-113.

For all images shown cells were trypsinized from polycarbonate cultures plated at 1:2 and grown for 7 days then plated at 2× confluent density on FBS treated Lab Tek 11, CC2 glass chamber slides (Nunc) or Transwell® filters (Product #3413) as stated in figure legends. Cells were grown 3 days then switched to differentiation media for 2 days prior to the beginning of experiments.

Cultures were maintained at 5% $CO_2$ and 37° C.

Expression Constructs and Transient Transfection:

Mouse occludin ATCC #MGC-5797 was cut with BsaA1 in the second extracellular loop and BclI in the 5' UTR and inserted in pFLAG-CMV-1 (Sigma), placing it downstream of secretory signal peptide and N-terminal FLAG epitope tag (FΔOcc). F-ΔOcc or pFLAG-CMV-1-BAP construct (Sigma) were transfected into cells using FuGENE® HD (Roche). Cells were plated in the morning at confluent density, transfected in the evening, and transfection media was replaced with differentiation media the following morning. pFLAG-CMV-1-BAP is the identical vector encoding secretory, N-terminal FLAG tagged, bacterial alkaline phosphatase.

Adenoviral Synthesis and Transduction:

The F-ΔOcc was cut out of pFLAG-CMV-1 using available restriction enzyme sites and used to construct an adenovirus (Ad-F-ΔOcc) following the AdEasy system. See, for example, He T C et al., *Proc. Natl. Acad. Sci. USA*, 1998, 95, 2509-2514. GFP only adenovirus and Ad-F-ΔOcc were titered together by transducing CIT3 monolayers and counting GFP positive cells at 9 hours post transduction. Adjusted viral stocks were used at equal effective titers.

Western Blotting:

Cells were lysed for 1 hour 40 then scraped in 50 mM tris pH 6.8, 2% SDS, 20% glycerol, 2.5 mM DTT, containing phosphatase inhibitor cocktail (cat.#P2850, Sigma) and protease inhibitor cocktail (cat.#P8340, Sigma) both 1:200. Lysate was passed through a tuberculin syringe and centrifuged 30 minutes at 16,000 rcf, 4° C. 40 µg supernatant protein per sample was separated (10-20% gradient gels Bio-Rad). Gels were transferred onto nitrocellulose and antibody stained. Stained blots were visualized using HRP-anti-host IgG (Pierce) with enhanced chemiluminescence (Amersham).

Peptide Synthesis:

Synthesis of linear CLYHYC (SEQ ID NO:4) and CDFYNPC (SEQ ID NO:5) was accomplished by using Fmoc chemistry. Assembly of side-chain protected N-α-Fmoc amino acids (AAs) was carried out on a resin support. Acylation reactions were carried out for 2 hours using 3-fold excess of Fmoc-AAs activated with N,N'-diisopropylcarbodiimide (DIC) in the presence of N-Hydroxybenzotriazole (HOBt). The N-terminal Fmoc group was removed with 20% piperidine in N,N-Dimethylformamide. Linear peptide was cleaved from the fully dried peptide-bound resin with freshly prepared TFA solution (TFA 94%, water 2.5%, ethanedithiol 2.5%, triisopropylsilane 1%) for 2.5 hours under nitrogen atmosphere then cyclized with 5% iodine in methanol and purified to 95% pure cyclic H-CLYHYC-OH by reverse phas HPLC. Peptide mass was confirmed by MALDI-TOF mass spectrometry (expected [M+H]+799.9, found 799.8). Cyclic H-CLYQYC-OH and H-CDFYNPC were made using the same process as described above except that H was replaced by Q. Peptide mass was confirmed by mass spectrometry (expected $[M+H]^+$=790.9, found 790.6).

The all D-form of peptide, e.g., CDFYNPC (SEQ ID NO:5), with a N-terminal amino group and a C-terminal carboxyl group was prepared by solid-phase peptide synthesis using Fmoc Chemistry on pre-loaded Fmoc-D-Cys-Wang resin, substitution of 0.5 mmol amino acid/g. The side-chain protecting groups on the following amino acids were used Cys(Trt), Asp(OtBu), Asn(Trt), Tyr(tBu). A 5 molar excess of Fmoc-D-amino acid, HOBt and DIC was used for coupling. Completion of the coupling was checked with the Kaiser test. Deprotection of the N-terminal protecting group was normally achieved by piperidine (20%) in DMF. Cleavage and removal of protecting groups was with TFA/water/ethanedithiol/triisopropylsilane as scavengers (90:5:2.5:2.5).

Peptide Purification

Crude peptide was purified by reversed-phase HPLC with a linear AB gradient where eluent A was 0.2% aqueous TFA and eluent B was 0.18% TFA in acetonitrile. Column used was Zorbax SB-300 C18, 9.4 mmI.D.×250 mm. Pure fractions were pooled, lyophilized and characterized by electrospray mass spectrometry (Perseptive Biosystems Mariner Biospectrometry work station) and analytical reversed-phase HPLC (Agilent 1100 series liquid chromatograph). The purification protocol is described in detail by Chen et al. in *J. Chromatography A*, 2007, 1140, 112-120.

Formation of the Disulfide Bond

Air oxidation of the cysteine residues to form the intrachain disulfide bond was achieved by stirring the peptide at room temperature in 0.1 M ammonium bicarbonate, pH 8.0, at a peptide concentration of 0.5 mg/mL for 18 hours. The reaction was monitored by analytical reversed-phase HPLC. The oxidized peptide had a lower retention time than the reduced form. Upon completion of disulfide bond formation, the solution was lyophilized and reophilized twice from water to remove the ammonium bicarbonate. The oxidized peptide was used without further purification.

Peptide Treatment

Peptides were solubilized in 30% DMSO in water just before the experiment. Cells were treated with 10 µM-5 mM of peptide for 2-16 hours at 37° C.

Activated Caspase Stains:

Cells were stained with Image-iT®LIVE Green Caspase-8 Detection Kit, Molecular Probes and/or Image-iT®LIVE Red Caspase-3 and -7 Detection Kit, Molecular Probes. Stains were both diluted into differentiation media that contained LYHY (SEQ ID NO:1) or LYQY (SEQ ID NO:3). Cells were stained in the incubator 1 hour, rinsed in 40 differentiation media, and processed for immunofluorescence.

Caspase-9 and Caspase-8/10 Inhibition:

Caspase-9 inhibitor (available from, e.g., R&D systems, Minneapolis, Minn., Cat.#FMK008) 100 µM, or both caspase-8 inhibitor (Cat.#FMK007) 50 µM and caspase-10 inhibitor (Cat.#FMK009) 50 µM (R&D systems) were dissolved into media and placed on cells for 2 h incubation. LYHY (SEQ ID NO:1) peptide was then applied at 300 µM with inhibitors for 2 hours total. Caspase-3 staining was performed during the last hour of LYHY (SEQ ID NO:1) treatment.

TUNEL Staining:

TUNEL staining was performed using the Roche In Situ Cell Death Detection Kit, TMR red. Cells were fixed in 2% paraformaldehyde and permeabilized in 1% sodium citrate (trisodium salt) containing 0.1% TX-100. Staining was performed as per manufacturers instructions.

Cells and Cell Culture:

CIT3 mouse mammary epithelial cells were grown as described by Toddywalla V S et al., *J. Pharmacol. Exp. Ther.*, 1997, 280, 669-676. To differentiate cells, this growth medium was modified by removal of EGF and addition of 3 µg/ml each of ovine prolactin and hydrocortisone (differentiation media).

EPH4 mouse mammary epithelial cells were grown as described by Reichmann E. et al., *J. Cell Biol.*, 1989, 108, 1127-1138. To differentiate cells, this growth medium was modified by addition of 3 µg/ml each of ovine prolactin and hydrocortisone (differentiation media).

MDCK cells were grown in MEM with 2 mM L-glutamine and Earle's BSS adjusted to contain 1.5 g/L sodium bicarbonate, 0.1 mM non-essential amino acids, 1.0 mM sodium pyruvate, and 10% FBS. To differentiate cells, this growth medium was modified by addition of 3 µg/ml each of ovine prolactin and hydrocortisone (differentiation media) to that described by Peixoto E B et al., *Cell Biol. Int.,* 2006, 30, 101-113.

For all images shown cells were trypsinized from polycarbonate cultures plated at 1:2 and grown for 7 days then plated at 2× confluent density on FBS treated Lab Tek 11, CC2 glass chamber slides (Nunc) or Transwell® filters (Product #3413). Cells were grown 3 days then switched to differentiation media for 2 days prior to the beginning of experiments.

Cultures were maintained at 5% $CO_2$ and 37° C.

Immunofluorescence

Apoptosis was measured by immunofluorescent analysis of active caspase-3. After peptide treatment, cells were fixed with 2% paraformaldehyde for 15 minutes at room temperature, permeabilized with 0.5% Triton-X100 for 5 minutes, and blocked in 2% BSA for 1 hour. Cells were then incubated for 1 hour with primary antibodies to cleaved caspase-3 (1:100, rabbit anti-cleaved caspase-3, Cell Signaling, Danvers, Mass., USA) and ZO-1 (1:50, rat anti-ZO-1, Jackson ImmunoResearch, West Grove, Pa., USA). Cells were then incubated for 45 minutes with secondary antibodies (1:100, donkey anti-rabbit-CY3 and donkey anti-rat-FITC, Jackson ImmunoResearch) and DAPI (Sigma. St. Louis, Mo., USA).

Imaging and Analysis

Some of the fluorescence were imaged with an Olympus 1×81 inverted motorized microscope with an attached spinning disk, using filter sets: DAPI EX:360-70 EM:420-60, FITC EX:450-80 EM:535, TRITC EX:535 EM:635. Total number of cell nuclei and number of cells positive for cleaved caspase-3 were counted and percent of cell population positive for caspase activity was calculated. Two regions of each treatment well were imaged and percentage of positive cells averaged. A total of 3-6 wells were averaged for each treatment to calculate mean±SEM.

Some of the images were collected, processed and analyzed using SlideBook software (Intelligent Imaging Innovations, Inc.) on a Nikon Diaphot TMD microscope equipped for fluorescence with a Xenon lamp and filter wheels (Sutter Instruments), fluorescent filters (Chroma), cooled CCD camera (Cooke) and stepper motor (Intelligent Imaging Innovations, Inc.). Adjacent z-sections were collected and deconvoluted using a nearest neighbors algorithm. Multi-fluor images were merged and renormalized.

Example 1

An adenovirus vector encoding a tight junction disrupting, N-terminally FLAG tagged, N-terminally truncated mouse occludin mutant (Ad-F-ΔOcc) (FIG. 1A) was constructed to determine the effect of occludin function disruption on apoptosis. FIG. 1A is a schematic general topology of occludin showing the mouse occludin sequence used to make tight junction disrupting constructs. Briefly, CIT3 cells were virally transduced to express dominant negative occludin. In FIG. 1A, COOH represents the C-terminus, PM=plasma membrane, F=FLAG epitope tag, and rs=restriction enzyme site used to make truncated occludin. LYHY (SEQ ID NO:1) was the conserved sequence used to make the inhibitory peptide for later experiments. The same figure also shows a truncated claudin sequence that produces mislocation of occludin as well as a peptide DFYNP (SEQ ID NO:2), derived from the second extracellular loop of several claudins that has the same effect.

The F-ΔOcc construct encoded by this virus was a dominant negative occludin and its expression in cultured epithelia cells caused lower transepithelial electrical resistance (TER) values and increased paracellular flux to small tracers. Further, gaps were found to have been induced in the P-face associated tight junction strands, as visualized by freeze-fracture electron microscopy. Ad-F-ΔOcc also encodes green fluorescent protein (GFP) as a separate, cytosolic protein under its own promoter, allowing simple identification of transduced cells.

Figure 1B:
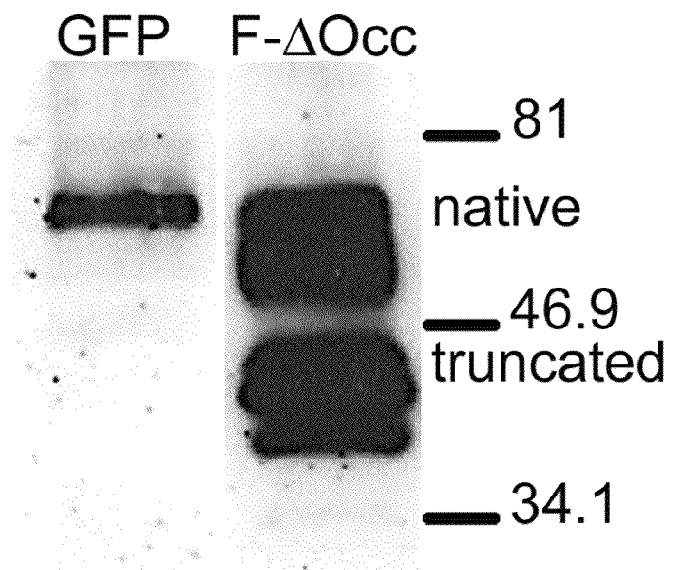
FIG. 1B is Western blots of endogenous and transduced truncated occludin 24 hours after transduction with either Ad-F-ΔOcc (F-ΔOcc) or Ad-GFP (GFP).

CIT3 and EPH4 mouse mammary epithelial cells were transduced with Ad-F-ΔOcc and yielded similar results. Most of the adenovirus experiments were performed in the CIT3 cell line because these cells showed higher transfection efficiency with plasmid expression constructs, allowing direct comparison of the transient transfection experiments (described below) with the adenovirus studies. Western blotting (see FIG. 1B) performed on lysate from newly confluent cells transduced with Ad-F-ΔOcc using an antibody detecting both truncated and endogenous occludin demonstrated that the native and truncated forms of occludin were seen in transduced cells and that both had a distribution of molecular weights. Lysates from cells transduced with identical adenovirus encoding only GFP (Ad-GFP) were processed in parallel as controls and appeared to show only one occludin band. FIG. 1B is Western blots of endogenous and transduced truncated occludin 24 hours after transduction with either Ad-F-ΔOcc (F-ΔOcc) or Ad-GFP (GFP). Blots were probed with an antibody against the C-terminus of endogenous occludin detecting both the native and truncated forms of occludin. Molecular weight in kilodaltons is shown to the right of the blots. As can be seen in FIG. 1B, most of the endogenous occludin in control samples ran at the same mobility as the uppermost band of occludin in the experimental lysates. Decreased occludin phosphorylation correlated with a shift of occludin to a faster migrating form and this shift in electrophoretic mobility correlated with reduced TER and with occludin displacement from tight junction strands into intracellular vesicles.

To determine effects of the localization of the transprotein on tight junction structure, mature monolayers of CIT3 cells were transduced with a low amount of Ad-F-ΔOcc to allow visualization of effects in individual cells. Cells were stained for ZO-1 to demonstrate the tight junctional network and for FLAG to label the transprotein. Immunofluorescence of transduced cells at 18 and 48 hours after application of Ad-F-ΔOcc was measured (date not shown). Some of the cells were stained with antibodies to FLAG and ZO-1 (data not shown), while some of the cells were stained with antibody to ZO-1 along and some were stained with antibody to FLAG alone (data not shown). Cells at 18 hours post transduction were rounded and transprotein could be seen at the cell border. By 48 h many transduced cells had a smaller perimeter and appeared to be extruding from the monolayer in what appears to be a morphology seen in epithelial cells destined for apoptosis. FLAG and ZO-1 were colocalized at the tight junction as intracellular punctata. The experiment shows F-ΔOcc expression disrupted occludin localization and electrophoretic mobility as well as the overall morphology of the tight junction.

Having established that F-ΔOcc expression disrupted occludin localization and electrophoretic mobility as well as the overall morphology of the tight junction, the effects of cells transduced with Ad-F-ΔOcc on apoptosis was examined. Cells were intentionally over-plated in order to rapidly and reproducibly form a confluent monolayer of high columnar cells and establish TER. Ad-F-ΔΔOcc or Ad-GFP was applied at equal effective titers when TER reached 300 Ohms·cm². TUNEL staining was performed to visualize apoptotic cells (data not shown). A large number of TUNEL stained cells was seen in cultures 48 hours after cells were transduced with Ad-F-ΔOcc, while very few were seen in the controls. Ad-F-ΔOcc transduced cells appeared to round up and dissociate from the monolayer almost entirely. Brightly TUNEL stained nuclei were frequently found in cells transduced with ad-F-ΔOcc at 48 hours following viral treatment (data not shown). These TUNEL reactive nuclei appeared to be ejected, at some point, from transduced cells.

The observation that F-ΔOcc expressing cells were leaving the monolayer was supported by the finding that the number of Ad-F-ΔOcc transduced cells remaining in the monolayer was reduced by about three fold at 48 hours post transduction as compared to the control adenovirus. As can be seen in FIG. 2A, which is a graph of counts of remaining transduced cells (GFP positive) at 48 hours post transduction, cell loss was not accompanied by loss of TER. As shown in FIG. 2B, TER in Ad-GFP-transduced cells rose to an average of 528 Ohms·cm² while that of the Ad-F-ΔOcc-transduced cells rose to an average of 506 Ohms·cm² during the experiment.

As a further evidence of apoptosis, whole cell lysates were processed for western blotting 24 hours following transduction. As shown in FIG. 2C, both caspase-8 and caspase-3 were cleaved to the active forms in cells transduced with Ad-F-ΔOcc. In FIG. 2C, newly confluent CIT3 monolayers grown in multi well plates were transduced with Ad-F-ΔOcc (ΔOcc) or Ad-GFP (GFP) or not transduced (NT). Samples were processed for western blotting 24 hours following transduction. Antibodies detected both full length and cleaved forms of caspases-8 and 3. Lysate was examined from three samples for each condition and corresponds to the three lanes in the blots as labeled. Loading controls are the parental forms of the caspases in the upper panels. Lower panels show proteolytically activated fragments. Molecular weight of marker proteins in kilodaltons is shown to the left of the blots. As can be seen, it appears that adenoviral transduction of cultured mammary epithelial cells with a dominant negative mutant of occludin leads to initiation of apoptosis within 24 hours.

Lipid mediated transient transfection of CIT3 and EPH4 cells to express the same construct (F-ΔOcc) as in adenovirus was performed to eliminate a possibility that the effects observed with adenoviral constructs were produced by the adenovirus itself and not the construct. Because there was no GFP reporter in these experiments, the results could also be used to rule out effects of GFP itself. A construct with a flag tagged truncation of claudin was used in similar experiments with similar results.

CIT3 cells were transiently transfected with F-ΔOcc and processed for immunofluorescence 18 hours later. An antibody to ZO-1 outlines junctional complexes and an antibody to FLAG labels a transduced cell. Panels of the composite image are stained (data not shown). As in the Ad-F-ΔOcc transduced cells, F-ΔOcc transprotein colocalized with ZO-1 at the tight junction at 18 hours post transfection. Transprotein was also seen in intracellular punctata. ZO-1 staining showed normal tight junctional distribution and was additionally more prevalent in the cytoplasm in transduced cells compared to neighboring, non-transduced cells.

In order to determine if apoptosis was increased in F-ΔOcc transfected cells, TUNEL staining and immunostaining against the FLAG tag were performed 48 hours post transfection (data not shown). Briefly, an immunofluorescence image were taken of CIT3 cells grown on glass slides that were transiently transfected with FLAG-bacterial alkaline phosphatase as a control or F-ΔOcc and processed 48 hours following transfection (data not shown). Monolayers were stained for TUNEL (red), FLAG (green), and nuclei (blue) (data not shown). At this time, 25% of control-transfected cells and 60% of F-ΔOcc-transfected cells were TUNEL positive (data not shown).

Similar results were obtained with the EPH4 cell line, however, these cells did not transfect with high efficiency (not shown). At 48 hours post transfection, the majority of F-ΔOcc-transfected cells were in various stages of extrusion and/or cellular deconstruction. Transfected cells in the process of epithelial extrusion were visualized by staining for FLAG epitope tag, actin, myosin, and nuclei. In an occasional view, an extrusion stalk was seen extending basally to the monolayer. Nuclei in extruding cells often were TUNEL negative. Extremely condensed, TUNEL positive nuclei were present in many other transduced cells that appeared to contain very little cytoplasm. Control cells were transfected with the same vector encoding bacterial alkaline phosphatase with identical FLAG tag and secretory peptide sequences (F-BAP). Cells that expressed F-BAP maintained normal morphology and were usually TUNEL negative. Cell extrusion was accompanied by condensation of an actinomyosin extrusion complex. An F-ΔOcc-transfected cell was seen rising above the plane of the epithelium with a condensed but non-fragmented nucleus. A condensed ring of actin and myosin was visible at the level of the apical junction complex and below the plane of the nucleus in the extruding cell. The results indicated that many F-ΔOcc-transfected cells had been removed entirely from the monolayers by 48 hours post-transduction and were unavailable for assessment of apoptosis by TUNEL staining. These results show that the expression of a truncated form of occludin in mammary cell monolayers leads to apoptosis and extrusion of expressing cells from the monolayer.

Peptide mimics of the second extracellular loop of occludin have been shown to disrupt occludin function and tight junction physiological properties in cultured cells and to disrupt the normal physiological properties of tight junctions in animals. To determine if disruption of occludin function via a function blocking peptide leads to apoptosis, mature monolayers of epithelial cell lines were treated with small inhibitory peptides against the second extracellular loop of occludin or claudin.

The peptide used in this study comprised the LYHY (SEQ ID NO:1) sequence found in the second extracellular loop of occludin in many mammals including mouse and dog or the DFYNP (SEQ ID NO:2) sequence found in the second extracellular loop of many claudins. To improve stability, the peptide was cyclized by reducing the flanking cysteine residues at both its C and N termini to form a disulfide bond.

Figure 3B:
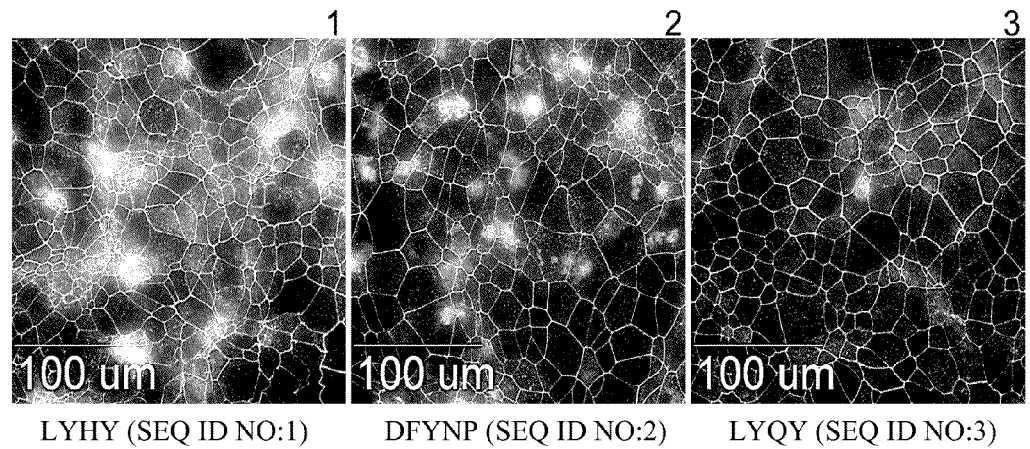
FIG. 3B is a stained image showing distribution of occludin in EPH4 cells treated with the occludin peptide (LYHY (SEQ ID NO:1)), the Claudin peptide (DFYNP (SEQ ID NO:2)) or a control peptide (LYQY (SEQ ID NO:3)).

To confirm that the LYHY (SEQ ID NO:1) and DFYNP (SEQ ID NO:2) peptides disrupted tight junction properties, a "calcium switch" experiment was performed. The removal of extracellular $Ca^{+2}$ and $Mg^{+2}$ abolished TER and disrupts intercellular junctions when applied to various epithelia, causing an intracellular redistribution of various cell adhesion proteins, including occludin, away from the apical junction complex. Several epithelial cell lines reorganized the apical junction complex and recovered TER following the replenishment of normal $Ca^{+2}$ and $Mg^{+2}$ containing medium. The calcium switch was performed on filter-grown EPH4 cells that had achieved a TER of 1000 Ohms·cm². After 15 minutes in $Ca^{+2}$ and $Mg^{+2}$ depleted-medium, TER was reduced to baseline resistance. Cells were then switched back to normal medium containing the occludin peptide, the claudin peptide or the control peptide at a concentration of 350 µM. The control peptide (LYQY (SEQ ID NO:3)) had one amino acid substitution of the occludin peptide and was also circularized with cysteines at each terminus. Peptides were removed after 24 hours. Control peptide-treated cells recovered initial TER by 48 h and the TER continued to climb, reaching 4000 Ohms·cm² after about 6 days. See FIG. 3A, which is a plot of transepithelial resistance (TER) recovery following the calcium switch. The "calcium switch" was applied to filter grown EPH4 monolayers that had achieved TER of 1000 (Ohms·cm²). Removal of calcium and magnesium reduced TER to the baseline of about 66 (Ohms·cm²). Occludin second extracellular loop peptide (LYHY (SEQ ID NO:1)) or control peptide (LYQY (SEQ ID NO:3)) were diluted into normal calcium and magnesium growth medium at 350 µM and placed in the tops and bottoms of the filter supports. TER was measured at 12 and 24 hours following peptide application. Peptides were washed away 24 hours following application and TER was measured every 24 hours thereafter. The inset is an enlargement of the early portion of the larger graph. As can be seen in FIG. 3A, both the occludin and the claudin peptides severely retarded TER recovery during the 24 hours it was present in the medium (see inset in FIG. 3A), although once removed TER began to climb in parallel with the control. All filters eventually reached a TER of 4000 Ohms·cm² several days following peptide removal.

To establish the effect of LYHY (SEQ ID NO:1) and DFYNP (SEQ ID NO:2) peptide treatment upon the distribution of endogenous occludin, EPH4 cells were treated with the peptides for 8 hours. The effect of peptides on occludin distribution in mature EPH4 cell monolayers is shown on FIG. 3B, where cell cultures grown on glass slides were treated with LYHY (SEQ ID NO:1), DFYNP (SEQ ID NO:2) or control LYQY (SEQ ID NO:3) peptide for 8 hours at 350 µM. Cells were then stained for occludin. Immunofluorescence using an antibody against the C-terminus of occludin showed islands of cells with irregular occludin distribution randomly distributed throughout the monolayers. Occludin was not as brightly stained at the tight junction in these cells and appeared in intracellular regions outside the tight junction. Only an occasional cell showing non-tight junctional distribution of occludin was observed in monolayers treated with the control peptide. Similar results were obtained with CIT3 and MDCK cells (data not shown).

Having established that LYHY (SEQ ID NO:1) and DFYNP (SEQ ID NO:3) peptides impeded recovery of TER following the calcium switch and changed the normal distribution of occludin, the effects of disruption of occludin function on apoptosis was examined. EPH4 mouse mammary epithelial cells and MDCK canine kidney epithelial cells were treated with LYHY (SEQ ID NO:1) peptide for various times and then TUNEL stained. In the case of both EPH4 and MDCK cells, LYHY (SEQ ID NO:1) peptide treatment increased TUNEL staining, indicating increased apoptosis. See FIG. 4A.

Figure 4A:
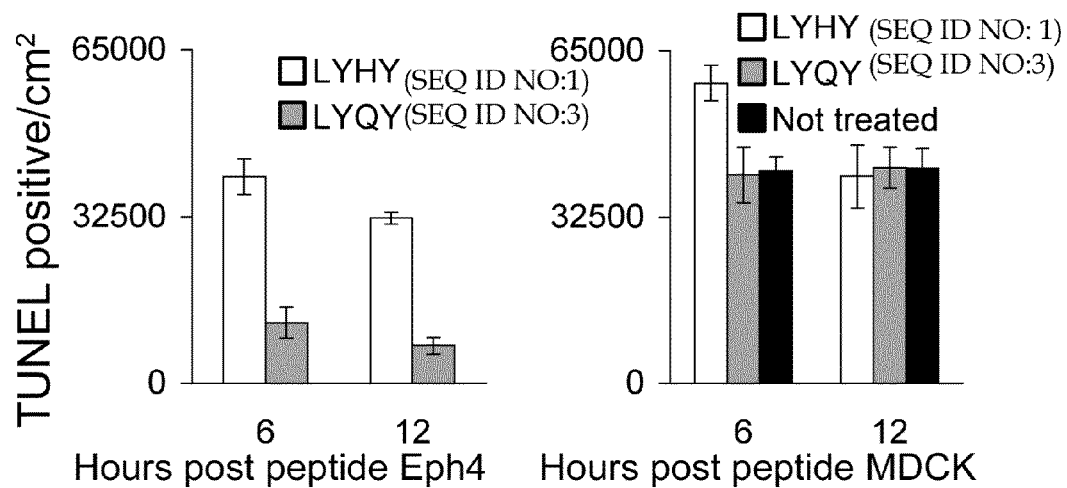
FIG. 4A is a graph showing the number of TUNEL stained EPH4 and MDCK cells that were grown on glass slides and treated with LYHY (SEQ ID NO:1) or control peptide for 6 or 12 hours.

FIGS. 4A and 4B show the effects of the LYHY (SEQ ID NO:1) peptide on TUNEL reactivity and TER. In particular, FIG. 4A is a graph showing the number of TUNEL stained EPH4 and MDCK cells that were grown on glass slides and treated with LYHY (SEQ ID NO:1) or control peptide for 6 or 12 hours. FIG. 4B is a graph of TER that was recorded at 0, 24, 28, and 72 hours post peptide treatment of EPH4 cells that were grown on filters until the TER reached 1000 (Ohms·cm²), then treated with solvent, LYHY (SEQ ID NO:1), or control peptides. Peptides were diluted to 350 µM in normal growth medium and placed in the top and bottom chambers. TER was recorded at 0, 24, 48, and 72 hours post peptide treatment. Peptides were replenished daily, after recordings. Similar results were obtained with the DFYNP (SEQ ID NO:2) peptide.

Although the LYHY (SEQ ID NO:1) and DFYNP (SEQ ID NO:2) peptides impeded the recovery of TER in EPH4 cells following the calcium switch, these peptides did not significantly reduce TER when added to the medium of intact, high resistance EPH4 monolayers. Peptide treatments of mature monolayers did not have a major effect on TER during 3 days of peptide treatment although the same treatments increased the apoptotic rate several fold (see FIG. 4B). Similarly, treatment of EPH4 cells with a larger occludin mimic peptide caused a change in occludin distribution while treated cells maintained the majority of control TER.

These results indicate that the LYHY (SEQ ID NO:1) and the DFYNP (SEQ ID NO:2) peptide treatments increase the rate of apoptosis. Possible mechanism linking occludin disruption to a known means of initiation of apoptosis was then explored using the LYHY (SEQ ID NO:1) peptide. It is believed that the loss of cellular adhesion results in the activation of the death receptor pathway and specify caspase-8 as the initiator caspase in apoptosis occurring due to loss of either cadherin or integrin function. To observe potential activation of the caspase-8 cascade, live EPH4 cells that had been treated with LYHY (SEQ ID NO:1) or control peptide were stained with cell permeable, fluorescent probes that irreversibly bind the proteolytic sites of activated caspase-8 (carboxyfluoresceine-LETD-fmk) and activated caspase-3 (sulphorhodamine-DEVD-fmk). At 2 h post LYHY peptide treatment, EPH4 cells showed increased staining for activated caspases relative to controls. Areas showing caspase-3 activation overlapped with areas showing caspase-8 activation, while caspase-8 activation was more widespread and sometimes occurred alone. Similar results were obtained with the DFYNP (SEQ ID NO:2) peptide.

FIGS. 5A and 5B show that LYHY (SEQ ID NO:1) peptide treatment increased activation of caspases 8 and 3, and that initiator caspase 8/10 inhibition inhibited activation of caspase-3 during occludin disruption. An immunofluorescence image was taken of mature EPH4 monolayers grown on glass slides that were treated with the LYHY (SEQ ID NO:1) peptide or with the control LYQY (SEQ ID NO:3) peptide at 350 µM for 2 hours and stained live during peptide treatment for activation of caspase-8 and caspase-3 (data not shown). The results indicate regions of caspase-8 activation with no apparent caspase-3 activation. FIG. 5A is a graph showing the number of EPH4 cells that showed caspase-8 and/or caspase-3 activation. FIG. 5B is a graph showing the number of EPH4 cells showing caspase-3 activation. Cells were grown on glass slides and pre-treated for 2 hours with inhibitors against caspases-8 and 10, or an inhibitor against caspase-9, or solvent only (not inhibited). Cells were then treated with LYHY (SEQ ID NO:1) peptide for 2 hours and assayed for caspase-3 activation as in FIG. 5A.

The activation of the downstream effector caspase-3 during inhibition of caspases 8 and 10 was recorded to determine the effects of occludin disruption on the death receptor pathway. It is believed that caspases 8 and 10 are the initiator caspases of the death receptor apoptotic pathway. Mature monolayers were incubated with no inhibitor or a combination of inhibitors of caspases 8 and 10 or the inhibitor of caspase-9. Monolayers were then treated with LYHY (SEQ ID NO:1) peptide and stained for activated caspase-3 to assay for inhibition of the potential initiator caspases. As shown in FIG. 5B, caspases 8 and 10 inhibition decreased the number of cells staining for activated caspase-3 by about 75%, an indication that disruption of occludin function leads to death receptor mediated apoptosis, and caspase-9 inhibition produced about a 20% drop in the number of cells staining for activated caspase-3. Caspase-9 is believed to be the primary initiator caspase for the mitochondrial pathway of apoptosis but is secondarily activated in the extrinsic pathway as well. Having established that inhibition of the death receptor initiator caspases-8 and 10 retarded the activation of caspase-3 during occludin disruption, the spatial orientation of activated caspases within the cell shortly following occludin disruption was then visualized.

EPH4 cells were treated with the LYHY (SEQ ID NO:1) peptide, and then stained for activated caspases 8 and 3 and with an antibody to occludin. As shown in FIG. 6, caspases 8 and 3 were activated in regions of disrupted tight junction strands during occludin disruption. FIG. 6 is an immunofluorescence image of mature EPH4 monolayers grown on glass slides that were treated with LYHY (SEQ ID NO:1) peptide at 350 μM for 2 hours and stained live during peptide treatment for activated caspase-8 and activated caspase-3. Cells were then fixed and stained for occludin and nuclei. Panels of the composite image are stained as labeled. Colocalization of activated caspase-8 and activated caspase-3 showed as yellow/orange. An immunofluorescence image was taken of EPH4 cells that were fixed and stained for occludin and the apical plasma membrane marker MUC1 as well as nuclei (data not shown). Two slightly different digital Z-sections were projected above and below the central XY image in this composite image. Two sets of white lines showed the plane of the upper and lower Z-sections, respectively (data not shown).

Referring again to FIG. 6, in this set of EPH4 cells, non junctional occludin staining can be seen at the apices of the two upper cells. In one cell, it appeared only caspase-8 was activated, where it localized with the non junctional occludin. Interestingly, both caspases were activated in the same region of one the neighboring cells, both localizing with non junctional occludin. As a means to further localize these regions of activated caspase-8 within the cell, digitally rendered Z-sections were constructed in cells treated identically but stained for activated caspase-8, occludin, and the apical membrane marker MUC1 (data not shown). Comparing its localization with that of occludin and MUC1, activated caspase-8 appeared to be localized at, and just basal to, the apical membrane of two adjacent cells in the region of junctional disruption. The lower Z projection in the occludin panel showed a "fuzzy" or diffusely occludin staining tight junction strand along the border of two cells that showed tight junctional disruption. The "fuzzy" strand was caught in the plane of the Z projection and it is possible that the activated caspase-8 was directly adjacent and additionally slightly basal to this disrupted tight junction strand.

Figure 7A:
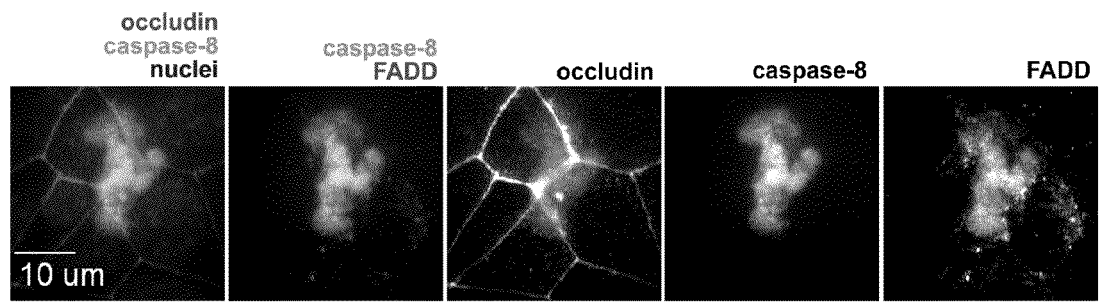
FIG. 7A is an immunofluorescence image of EPH4 cells that were stained live for activated caspase-8, occludin, the DISC adapter protein FADD and nuclei.
Figure 7B:
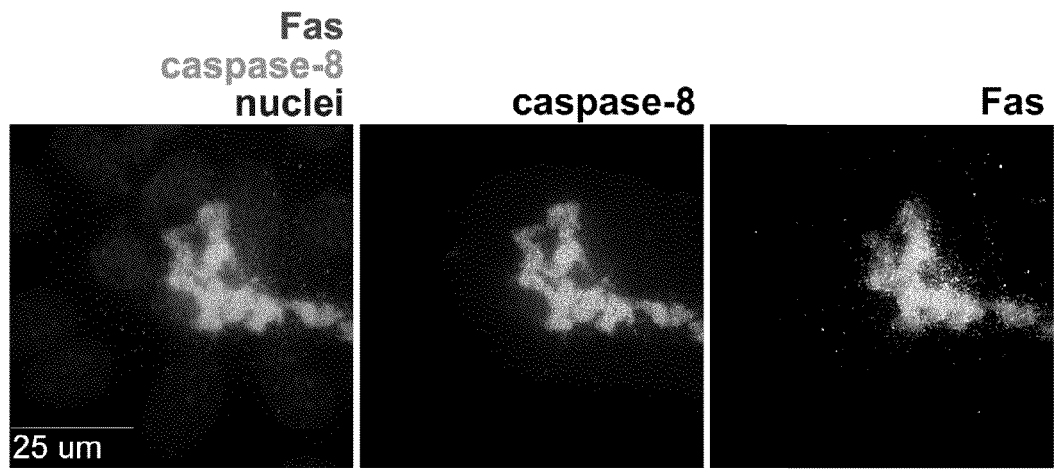
FIG. 7B is an immunofluorescence image of EPH4 cells that were stained live for activated caspase-8, Fas and nuclei.
Figure 7C:
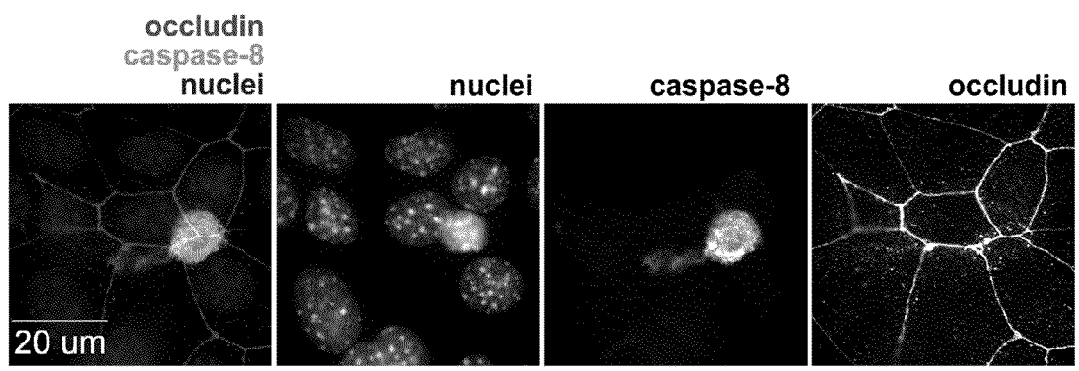
FIG. 7C is an immunofluorescence image of mature EPH4 monolayers grown on glass slides that were treated with LYHY (SEQ ID NO:1) peptide at 350 μM for 6 hours and stained live during the 6th hour of treatment for activation of caspase-8, occludin and nuclei.

Since disruption of occludin function led to activation of the initiator caspase-8, it was believed that the death inducing signaling complex (DISC) would form, which includes the caspase-8 binding protein FADD, one or more death receptor proteins, and activated caspase-8 in those cells showing displacement of occludin from tight junction strands. Accordingly, LYHY (SEQ ID NO:1)-treated cells were stained live for activated caspase-8 and then fixed and stained with antibodies against FADD, Fas death receptor, and occludin. As shown in FIGS. 7A to 7C, activated caspase-8 was again enriched in regions showing non junctional occludin.

FIGS. 7A to 7C show that activated caspase-8 localized with displaced occludin and DISC proteins during occludin disruption. Extruding cells showed caspase-8 activation during occludin disruption. FIG. 7A is an immunofluorescence image of EPH4 cells that were stained for activated caspase-8, occludin, the DISC adapter protein FADD and nuclei. Panels in the composite image were stained as labeled. FIG. 7B is an immunofluorescence image of EPH4 cells that were stained for activated caspase-8, Fas and nuclei. Panels in the composite image were stained as labeled. And FIG. 7C is an immunofluorescence image of mature EPH4 monolayers grown on glass slides that were treated with LYHY (SEQ ID NO:1) peptide at 350 μM for 6 hours and stained live during the 6th hour of treatment for activation of caspase-8, occludin and nuclei. Panels in the composite image were stained as labeled.

As can be seen in FIG. 7A, the cytoplasmic scaffolding protein FADD was enriched in regions showing non junctional occludin. The transepithelial death receptor CD95/Fas was localized in regions showing caspase-8 activation as shown with a mouse monoclonal antibody. See FIG. 7B. Many cells showing caspase-8 activation were extruded and showed tadpole morphology several hours following application of LYHY (SEQ ID NO:1). See FIG. 7C. The nucleus of the extruding cell had risen above the plane of the epithelium and appeared somewhat out of focus in relation to the more basal surrounding nuclei. The nucleus of the extruding cell was somewhat condensed, but otherwise intact, a result similar to cells expressing truncated occludin.

Without being bound by any theory, these results appear to indicate caspase-8 activation as the initiation mechanism for apoptosis brought about by the occludin and the claudin disrupting peptides. In addition, these results indicate that DISC proteins aggregate and serve to activate caspase-8 in cellular regions showing breakdown of tight junctional architecture and the presence of non junctional occludin.

Example 2

Representative Peptides

Below is a list of some of the peptides that have been studied (peptide numbers 1-5, respectively, where peptides 1, 3, 4, and 5 are L-amino acids and peptide 2 is D-amino acid):

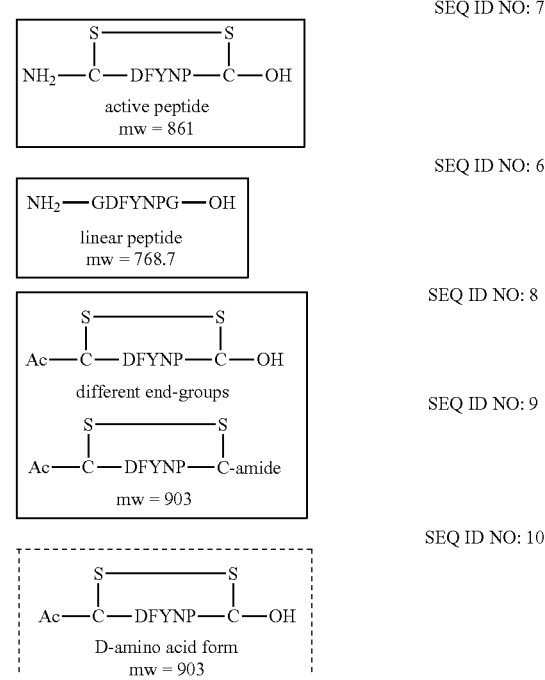

Results of 2 mM Peptides Overnight

Figure 8:
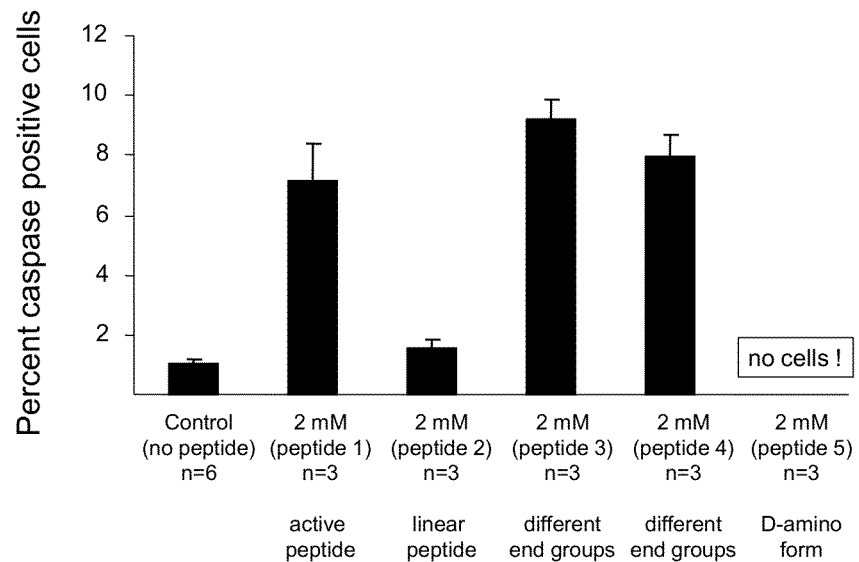
FIG. 8 is a graph of percent caspase positive cells after treatment with 2 mM of each of the peptides 1-5 and a control solution.

EPH4 cells were treated with 2 mM of each of the peptide (peptides 1-5 above). EPH4 cells were also treated with a control solution. The results are shown in a graph form in FIG. 8. The graph represents averaged 2 regions for each well and averaged 3 different wells for each peptide. As can be seen, none of the cells that were treated with peptide 5 (D-amino acid form) had caspase activity.

Peptide 5 at Shorter Times

Figure 9:
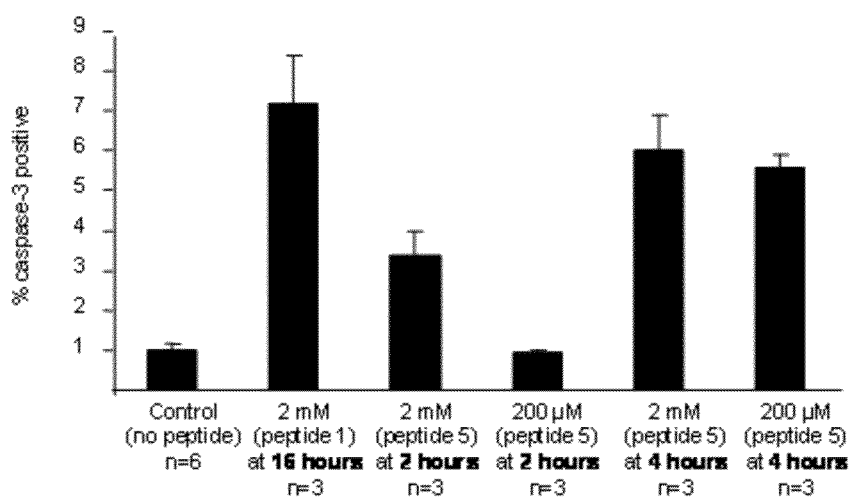
FIG. 9 is a graph of percent caspase positive cells after treatment with various concentrations of Peptide 5 at different hours, 2 mM of peptide 1 at 16 hours, and a control solution.
Figure 10:
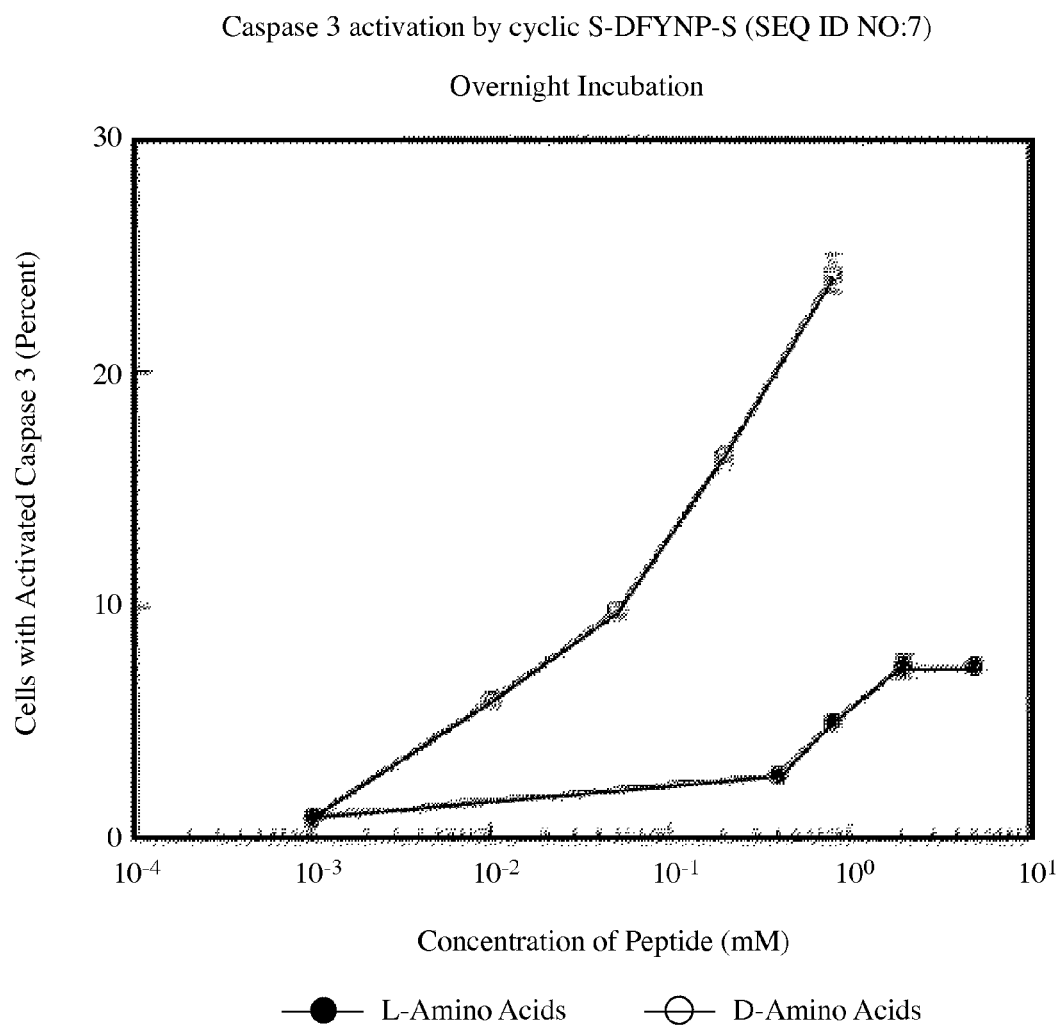
FIG. 10 is a dose-response curve for the effects of the D- and L-amino acid forms of the peptide.

The above experiment was repeated with Peptide 5 at various hours and concentrations along with control and with Peptide 1 at 2 mM for 16 hours. The results are shown in FIG. 9, which represents averaged 2 regions for each well and averaged 3 different wells for each concentration. FIG. 10 shows a comparison of the dose response curves for the L-(peptide 1)-amino acid and the D-(peptide 5)-amino acid forms of the peptide.

DISCUSSION

Using occludin-disrupting tools to disrupt occludin function in three epithelial cell lines showed that this disruption increased apoptosis in treated cells. Apoptotic cells were lost from the monolayer with no significant change in TER. In addition, movement of occludin out of the junctional complex in response to an occludin peptide mimic led to activation of caspase-8 in these same regions that were enriched in displaced occludin and DISC proteins.

The above experiments show that otherwise normal epithelial cells that are unable to form, or that lose, any of the more widely studied forms of cellular attachments undergo apoptosis. Without being bound by any theory, it is believed that disruption of integrin-mediated cell-to-substratum attachment, disruption of cadherin-mediated adherence junctions, and disruption of connexin-mediated gap junctions all stimulate apoptosis. These apoptotic responses to the disruption of cellular attachments provide an adaptive advantage to the host allowing epithelia to remove malfunctioning cells.

Occludin is a tight junction adhesion protein that is believed to provide cell-to-cell adhesion. The present inventors have shown that disruption of a tight junction adhesion protein (such as occludin and claudin) function in confluent epithelial monolayers leads to apoptosis.

Truncated Occludin Expression

Salivary cell lines were created expressing low levels of the F-ΔOcc construct. These cells exhibited normal distribution of endogenous occludin, ZO-1, and JAM and showed normal tight junction structure. Tracer flux was increased and TER decreased. In this study cells expressed low levels of the transprotein relative to endogenous protein and did not induce frank tight junction disruption. In addition, the cell lines were constitutively expressing cells that were stably transfected and selected for survivorship. It is well known that some polarized epithelial cells do survive the loss of tight junction adhesion. This survival is believed to be abnormal and pathological.

Cells used in the present disclosure were naïve to transprotein expression and staining for ZO-1 demonstrated frank tight junction disruption in expressing cells.

Extrusion and TER

Cells expressing dominant negative occludin appeared to migrate out of the monolayer prior to becoming TUNEL positive. Many of the occludin peptide treated cells that showed non junctional occludin distribution and caspase-8 activation also showed the distinctive morphology of cellular extrusion. The finding that the several fold increase in apoptosis, which occurred both in peptide disruption and dominant negative occludin expression studies, did not decrease the trans-epithelial resistance suggests that cell loss proceeds by an orderly biological process that maintains rather than disrupts epithelial barrier properties. Similarly, cultured monolayers of intestinal epithelial cells were able to maintain 50% of basal TER when treated with a Fas crosslinking antibody that led to the loss of half of the cells in the culture in only 24 hours.

Physiological Relevance

Peptide treatments affected some of the cells in the confluent monolayers. Occludin peptide caused occludin to stain in intracellular, punctate, nonjunctional patches in islands of cells throughout the monolayers, while the majority of treated cells showed normal occludin localization. In several experiments, dominant negative occludin was expressed in only a minority of cells. These conditions are believed to mimic loss of occludin function in otherwise normal epithelial cells that are spatially unable to form or maintain occludin binding or have undergone any cellular dysregulation disruptive of occludin function, indicating that an endogenous pathway is triggered to remove epithelial cells unable to maintain occludin function.

Loss of Adhesion and Apoptotic Initiation

The present inventors have shown that disruption of occludin or claudin function initiates the death receptor pathway of apoptosis. It is believed that elements of the death receptor or extrinsic apoptotic pathway may function generally to trigger apoptosis in epithelial cells that have lost normal cell-cell or cell stromal attachments. The present disclosure also shows the formation of a specific caspase-containing complex during loss of normal cellular attachment occurring prior to changes that lead to nuclear condensation and cell extrusion.

The localization of activated caspase-8 in regions of non junctional occludin suggests that displaced occludin may act to promote caspase-8 activation, as appears to be the case for unligated integrin in detachment-induced apoptosis or anoikis. The Akt antagonist, lipid phosphatase PTEN is another suitable molecule for linking loss of occludin function to apoptosis. It has been shown that the PIP3 phosphatase PTEN binds to the tight junction associated MAGI, PAR, and DLG proteins. The lipid phosphatase activity of PTEN correlates positively with the stability of the apical junction complex. Moreover, PTEN plays a role in activation of the death receptor pathway of apoptosis under various conditions. The present immunofluorescence study showed that PTEN is associated with the tight junction in cells (data not shown).

It is believed that one of the steps in the metastatic process is the loss of intercellular junctions without subsequent apoptosis. Without being bound by any theory, it is believed that the molecular pathway(s) linking adhesion protein (such as occludin and claudin) disruption to apoptosis is attenuated or altogether lost in epithelial cancers and that adhesion protein (e.g., occludin and claudin) dysregulation is linked to metastases. These pathways can be augmented by drug therapies to induce apoptosis or halt epithelial to mesenchymal transformation in particular in cells that have lost normal occludin based adhesion.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/ or equivalent structures, functions, ranges or steps are disclosed herein, and without intending to publicly dedicate any patentable subject matter.

What is claimed:

1. A method for modulating apoptosis of epithelial cells of a subject comprising administering to the subject a therapeutically effective amount of a tight junction protein modulator, wherein said tight junction protein modulator consists of the formula:

$G-Z^1-Z^2-Z^3-Z^4-Z^5-G$ (SEQ ID NO:11)

wherein

G is glycine;
$Z^1$ is aspartic acid, glutamic acid, asparagine, or glutamine;
$Z^2$ is phenylalanine, tyrosine, tryptophan, or leucine;
$Z^3$ is tyrosine, phenylalanine, tryptophan, or leucine;
$Z^4$ is asparagine or glutamine; and
$Z^5$ is proline.

2. The method of claim 1, wherein said tight junction protein modulator comprises D-amino acids.

3. The method of claim 2, wherein $Z^1$ is aspartic acid, $Z^2$ is phenylalanine, $Z^3$ is tyrosine, and $Z^4$ is asparagine.

4. The method of claim 3, wherein each amino acid is D-amino acid.

5. A method for removing at least a portion of epithelia cells that are in hyperplastic stages from a subject, said method comprising administering to the subject in need of such treatment a tight junction protein inhibitor, wherein said tight junction protein modulator consists of the formula:

$G-Z^1-Z^2-Z^3-Z^4-Z^5-G$ (SEQ ID NO:11)

wherein

G is glycine;
$Z^1$ is aspartic acid, glutamic acid, asparagine, or glutamine;
$Z^2$ is phenylalanine, tyrosine, tryptophan, or leucine;
$Z^3$ is tyrosine, phenylalanine, tryptophan, or leucine;
$Z^4$ is asparagine or glutamine; and
$Z^5$ is proline.

6. The method of claim 5, wherein $Z^1$ is aspartic acid, $Z^2$ is phenylalanine, $Z^3$ is tyrosine, and $Z^4$ is asparagine.

7. The method of claim 6, wherein each amino acid is D-amino acid.

* * * * *